(12) United States Patent
Bejarano et al.

(10) Patent No.: US 8,591,444 B2
(45) Date of Patent: Nov. 26, 2013

(54) HINGE FOR AN ORTHOPEDIC BRACE

(75) Inventors: Robert Bejarano, San Marcos, CA (US); Emee Villegas, Oceanside, CA (US); Carl Hoffmeier, Solana Beach, CA (US)

(73) Assignee: DJO, LLC, Vista, CA (US)

(*) Notice: Subject to any disclaimer, the term of this patent is extended or adjusted under 35 U.S.C. 154(b) by 0 days.

(21) Appl. No.: 13/169,863

(22) Filed: Jun. 27, 2011

(65) Prior Publication Data

US 2011/0314637 A1    Dec. 29, 2011

Related U.S. Application Data

(60) Provisional application No. 61/358,771, filed on Jun. 25, 2010.

(51) Int. Cl.
*A61F 5/00* (2006.01)

(52) U.S. Cl.
USPC .................... 602/16; 602/20; 602/23

(58) Field of Classification Search
USPC ............... 602/16, 20–28; 128/878–879, 882; 16/321, 334
See application file for complete search history.

(56) References Cited

U.S. PATENT DOCUMENTS

| | | | | |
|---|---|---|---|---|
| 4,846,842 A * | 7/1989 | Connolly et al. | ............... | 623/43 |
| 4,982,732 A * | 1/1991 | Morris | ............... | 602/16 |
| 5,814,000 A | 9/1998 | Kilbey | | |
| 6,993,808 B1 * | 2/2006 | Bennett et al. | ............... | 16/334 |
| 7,235,059 B2 * | 6/2007 | Mason et al. | ............... | 602/26 |
| 7,984,531 B2 * | 7/2011 | Moore | ............... | 16/326 |
| 2006/0155230 A1 * | 7/2006 | Mason et al. | ............... | 602/16 |
| 2007/0067957 A1 * | 3/2007 | Moore | ............... | 16/326 |

FOREIGN PATENT DOCUMENTS

FR    2 915 369    10/2008

OTHER PUBLICATIONS

International Search Report and Written Opinion of the International Searching Authority of Application No. PCT/US2011/042045 mailed Oct. 13, 2011.

* cited by examiner

*Primary Examiner* — Michael A. Brown
(74) *Attorney, Agent, or Firm* — Ropes & Gray LLP

(57) ABSTRACT

Systems, devices, and methods for adjusting rotational limits of an orthopedic brace hinge are provided. A hinge stop assembly limits rotational travel of first and second frame members of the hinge. An indexing key of the hinge stop assembly is actuatable in a direction parallel to the axis of rotation of the hinge to lock and unlock the position of the hinge stop assembly relative to the hinge. Actuation of the hinge stop assembly unlocks the indexing key and allows movement of the hinge stop assembly to set a desired limit on the flexion or extension of the brace hinge. Release of the hinge stop assembly locks the indexing key and locks the hinge stop assembly in place.

20 Claims, 11 Drawing Sheets

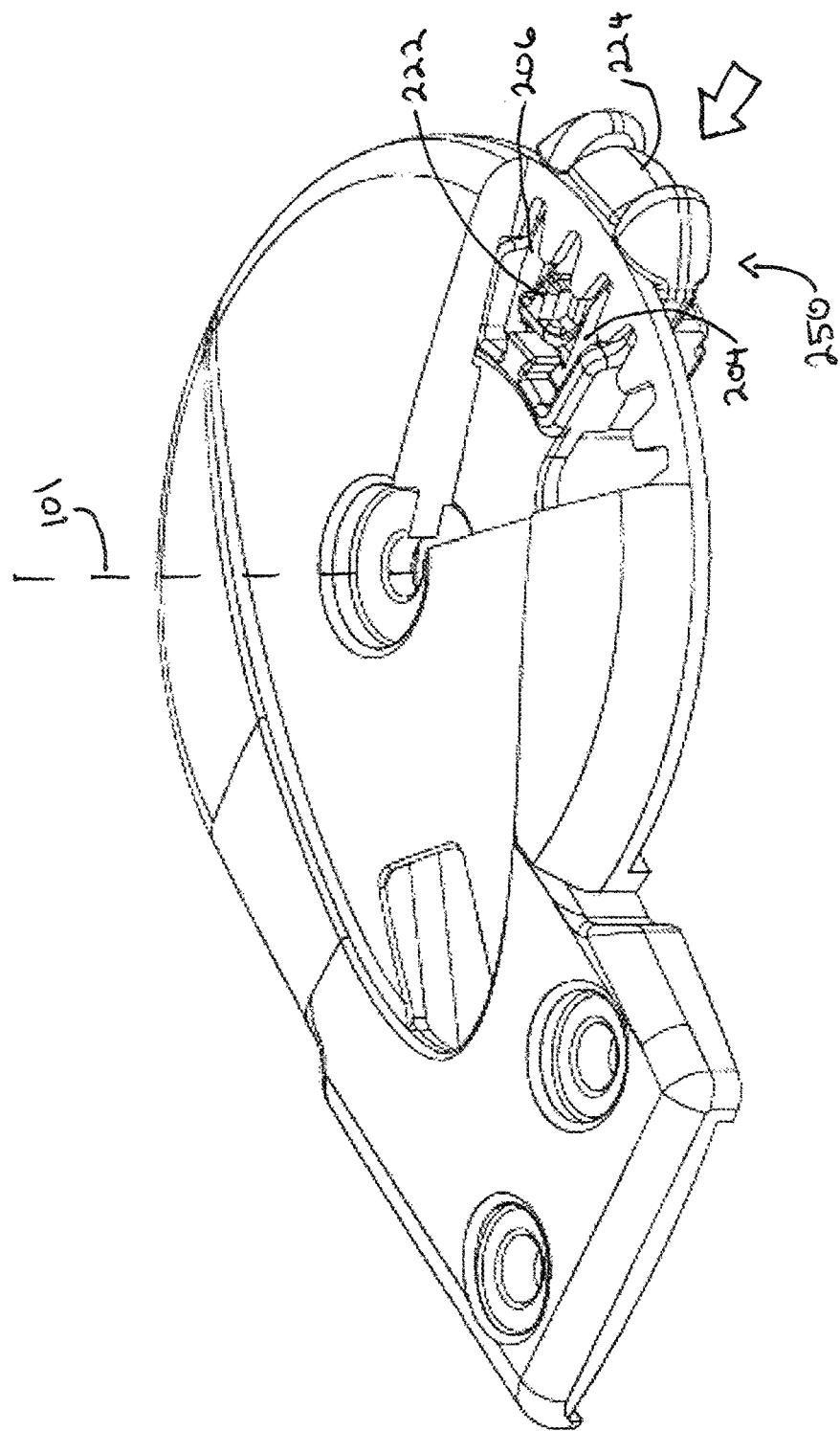

HINGE FOR AN ORTHOPEDIC BRACE

BACKGROUND

Orthopedic braces use hinge mechanisms that permit a patient to maintain joint flexibility while the brace still protects the injured body parts. Hinges for many braces are adjustable, with extension and flexion limiting mechanisms. Such limiting means may be adjustable to allow a patient or health care provider to set desired limits on flexion and extension of a joint. Limiting means may be different for a user to actuate and adjust to the desired limiting setting. Improved hinge adjustment mechanisms are accordingly needed.

SUMMARY

Disclosed herein are systems, devices, and methods for adjusting a brace hinge. A hinge stop assembly is included with an orthopedic brace to allow a user to set a limit on flexion or extension of an orthopedic brace. The hinge stop assembly locks in position on the hinge and prevents frame members from rotating beyond the position of the hinge stop assembly. An actuator button on the hinge stop assembly facilitates locking and unlocking of the hinge stop assembly and provides a user with easy adjustment of the rotational limiting features of the hinge.

In some embodiments, a hinge assembly for an orthopedic brace includes a hinge cover having a center rotation axis. The center rotation axis of the hinge cover may coincide with the center rotation axis of the hinge assembly. First and second frame members of the brace are pivotably connected to the hinge cover. At least one hinge stop assembly is operable with the hinge for limiting rotational travel of the first or second frame members. The hinge stop assembly includes an indexing key that is actuatable in a direction parallel to the center rotation axis of the hinge.

In some embodiments, a hinge assembly includes a hinge plate positioned between the hinge cover and at least one of the first and second frame members. A second hinge plate may be included in the hinge, and the first and second frame members may be positioned between the first and second hinge plates. The hinge plates have gear teeth that are configured to engage a hinge stop assembly of the hinge. In certain implementations, the indexing key of the hinge is configured to engage the gear teeth of a hinge plate. In certain implementations, a hinge stop assembly includes a hinge stop face that extends between first and second hinge plates for making contact with the first or second frame members. In certain implementations, a hinge includes a locking mechanism with a locking pin configured to engage gear teeth disposed on first and second hinge plates.

In some embodiments, a hinge stop assembly includes an upper housing having a pocket for receiving an actuator button. In certain implementations, an actuator button is actuatable in a direction parallel to the center rotation axis of a hinge. In certain implementations, an actuator button is actuatable in a direction perpendicular to the center axis of a hinge. An indexing key may include a ramp facing radially and angularly away from the center rotational axis of a hinge, and the indexing key may include a plurality of arms that fit within corresponding notches disposed within the hinge to form a hinge stop location to limit the angular rotational travel of the second frame member. The actuator button may include a platform that interfaces with the ramp and is actuatable to drive the ramp in a direction parallel to the central rotational axis of the hinge. In certain implementations, the indexing key and actuator are disposed between first and second hinge plates and are actuatable in a direction perpendicular to the central rotational axis of the hinge assembly. In certain implementations, a button and indexing key fit within a receptacle disposed between first and second hinge plates of a hinge.

In some embodiments, a method for adjusting rotation of an orthopedic braces is provided. In certain implementations, the orthopedic brace includes first and second frame members, a hinge having a center rotation axis, and a hinge stop assembly. The hinge stop assembly is actuated to cause an indexing key to move in a direction parallel to the center rotation axis of the hinge, and the hinge stop assembly is positioned around the hinge. The hinge stop assembly is released to cause the indexing key to move in a direction parallel to the center rotation axis of the hinge and lock the hinge stop assembly in position relative to the hinge.

In certain implementations, actuating a hinge stop assembly includes applying a force to an actuator button connected to the hinge stop assembly. The force may be applied to the actuator button in a direction perpendicular to the center rotation axis of the hinge, or may be applied in a direction parallel to the center rotation axis of the hinge. In certain implementations, positioning a hinge stop assembly includes moving the hinge stop assembly about a perimeter of a hinge plate.

BRIEF DESCRIPTION OF THE DRAWINGS

The following figures depict brace hinge mechanisms in which like reference numerals refer to like elements. These depicted embodiments may not be drawn to scale and are to be understood as illustrative but not as limiting.

FIG. 11 shows a hinge stop assembly after actuation.

DESCRIPTION OF EXEMPLARY EMBODIMENTS

The present disclosure relates to systems, devices and methods for adjusting a brace hinge. To provide an overall understanding of the principles disclosed, certain illustrative embodiments will now be described, as more particularly set forth in the figures. However, one of ordinary skill in the art will understand that the systems and methods described herein may be adapted and modified for other suitable applications, and that such other additions and modifications are within the scope hereof. For example, the devices and methods described herein may be used in a lower extremity brace (e.g., knee or leg or pelvic or hip brace) or an upper extremity brace (e.g., elbow or shoulder brace).

In particular, a hinge is provided for an orthopedic brace, the hinge including two frame members, a pivotal connector connecting the two frame members, a rotational limiting hinge, and a rotational locking mechanism. The rotational limiting hinge contains at least one adjustable rotational limiting mechanism that can be positioned at a desired angular location about the hinge. The adjustable rotational limiting mechanism is locked into position by engaging one or more set of gear teeth on the rotational limiting hinge. The adjustable rotational limiting mechanism includes a limiting face that contacts a corresponding face of one of the frame members that is allowed free rotation relative to the other frame member and the rotational limiting hinge.

Figure 1A:
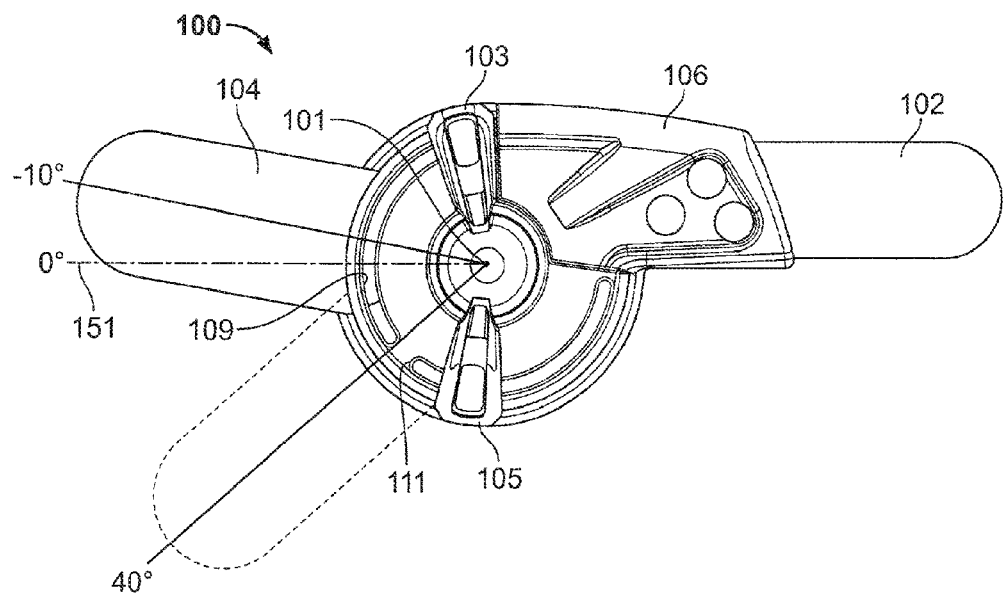
FIGS. 1A-1B depict top views of a hinge having first and second frame members and first and second hinge stop assemblies.

In certain implementations, as shown in FIG. 1A, two adjustable rotational limiting mechanisms are included that, when fixed in place, bind the free rotating frame member so it cycles only between the two mechanisms, at angular settings that are adjustably limiting.

Figure 1B:
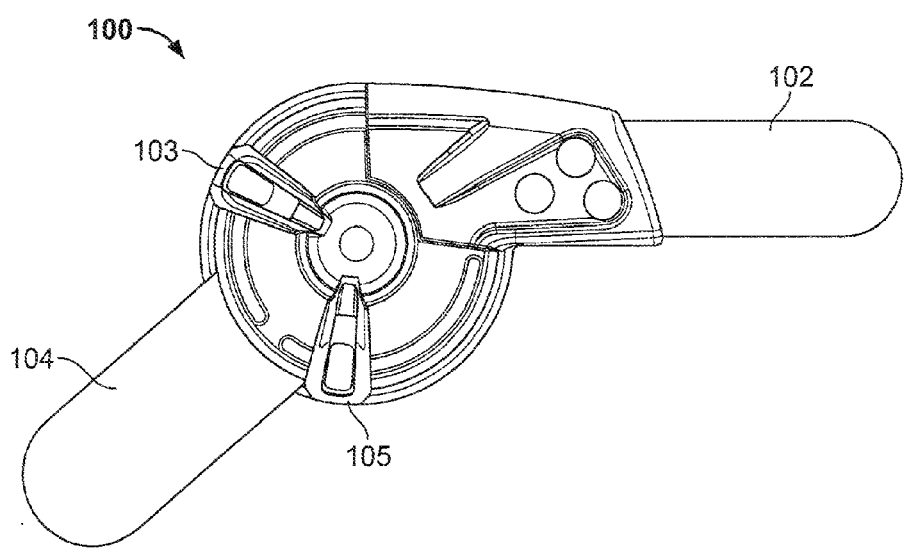

FIG. 1A shows a hinge 100 having a first frame member 102, a second frame member 104 rotatable about a center rotation axis 101, and a lateral hinge cover 106 for operatively connecting the two frame members 102 and 104. The hinge 100 also includes first and second rotational limiting mechanisms, shown as hinge stop assemblies 103 and 105, respectively, for limiting the angular motion of the second frame member 104. The hinge stop assemblies 103 and 105 are movable along rotation paths 109 and 111 which are defined within the hinge 106. The positions of the hinge stop assemblies 103 and 105 along the rotation paths 109 and 111 determine the allowed travel path for the second frame member 104 with respect to the first frame member 102. As shown in FIGS. 1A and 1B, the second rotating frame member 104 is movable between the first and second hinge stop assemblies 103 and 105. In addition the two hinge step assemblies can be adjusted to lock the free rotational frame member at a solitary angular setting, restricting any further angular motion of the free rotating frame member relative to the other frame member and the rotational limiting hinge.

Figure 2:
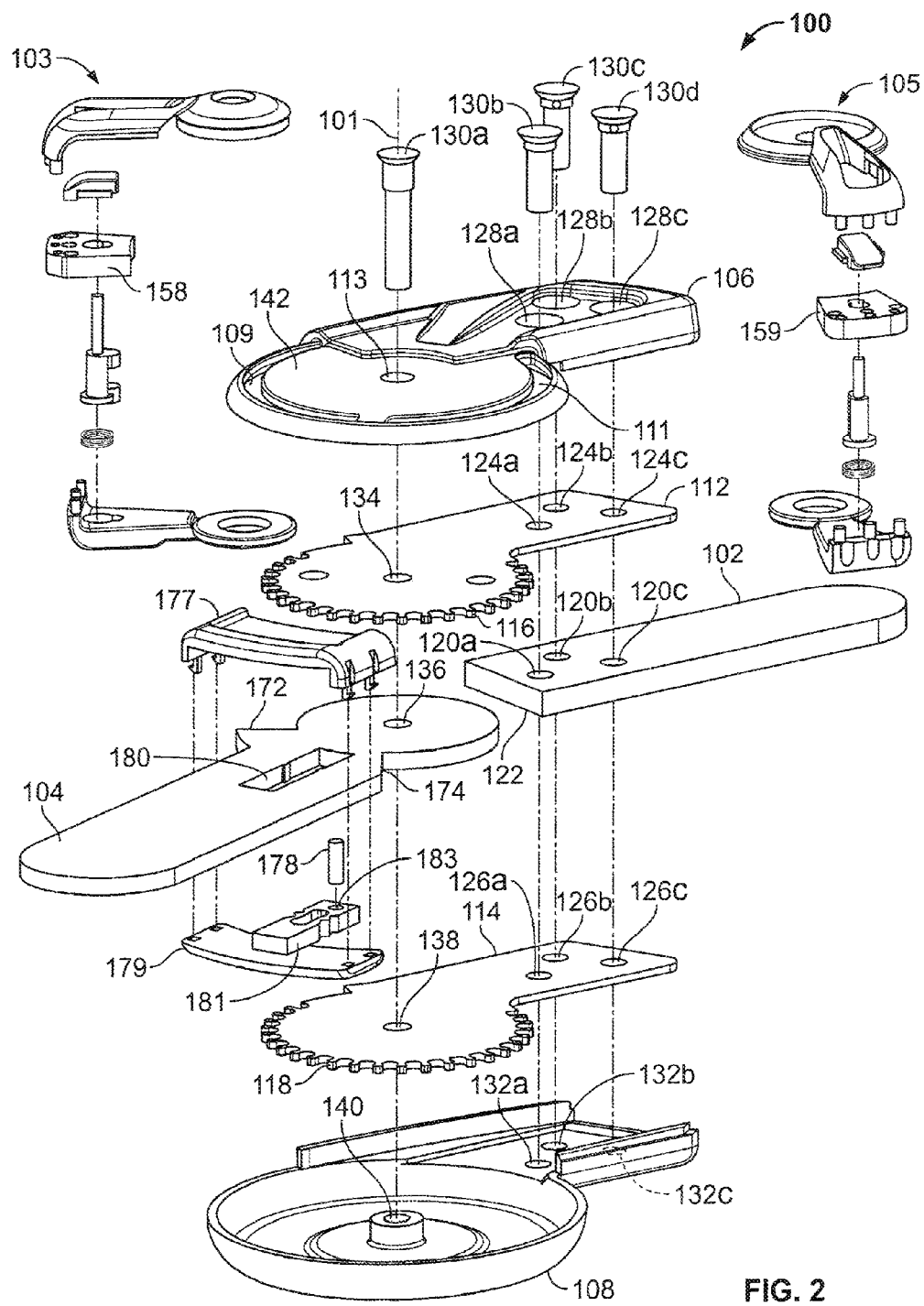
FIG. 2 shows an exploded view of the hinge of FIG. 1A.

FIG. 2 shows an exploded view of the hinge 100. As shown, the lateral hinge cover 106 and a medial hinge cover 108 enclose first and second frame members 102 and 104 and first and second hinge plates 112 and 114. The first and second frame members 102 and 104 are pivotally connected to one another. In some embodiments, the first and second frame members 102 and 104 are positioned along the lateral side of the user's thigh and calf, respectively. The first frame member 102 is stationary with respect to the lateral and medial hinge covers 106 and 108. As shown in FIG. 2, the first frame member 102 is positioned between the first and second hinge plates 112 and 114 and includes a plurality of holes 120a-120c near a distal end 122 for receiving a plurality of fasteners 130b-130d. The first and second hinge plates 112 and 114 also include a plurality of mating holes 124a-124c and 126a-126c, respectively, for receiving the fasteners 130b-130d. When assembled, the fasteners 130b-130d lock the first frame member 102 and the first and second hinge plates 112 and 114 to the lateral and medial hinge covers 106 and 108.

The second frame member 104 is pivotally engaged to the first and second hinge plates 112 and 114 via the fastener 130a. The second frame member 104 includes a mating hole 136 for receiving the fastener 130a. The second frame member 104 pivots about the fastener 130a and with respect to the first frame member 102 between the first and second hinge plates 112 and 114. As noted above, the second frame member 104 is also adapted to move between two hinge stop assemblies 103 and 105, which travel along the rotation paths 109 and 111, respectively. The hinge stop assemblies 103 and 105 are adapted to index and lock in a particular angular position for providing a range of motion window for the second frame member 104 to travel. The hinge stop assemblies 103 and 105 provide maximum flexion and extension travel stops for the second frame member 104.

Figure 3:
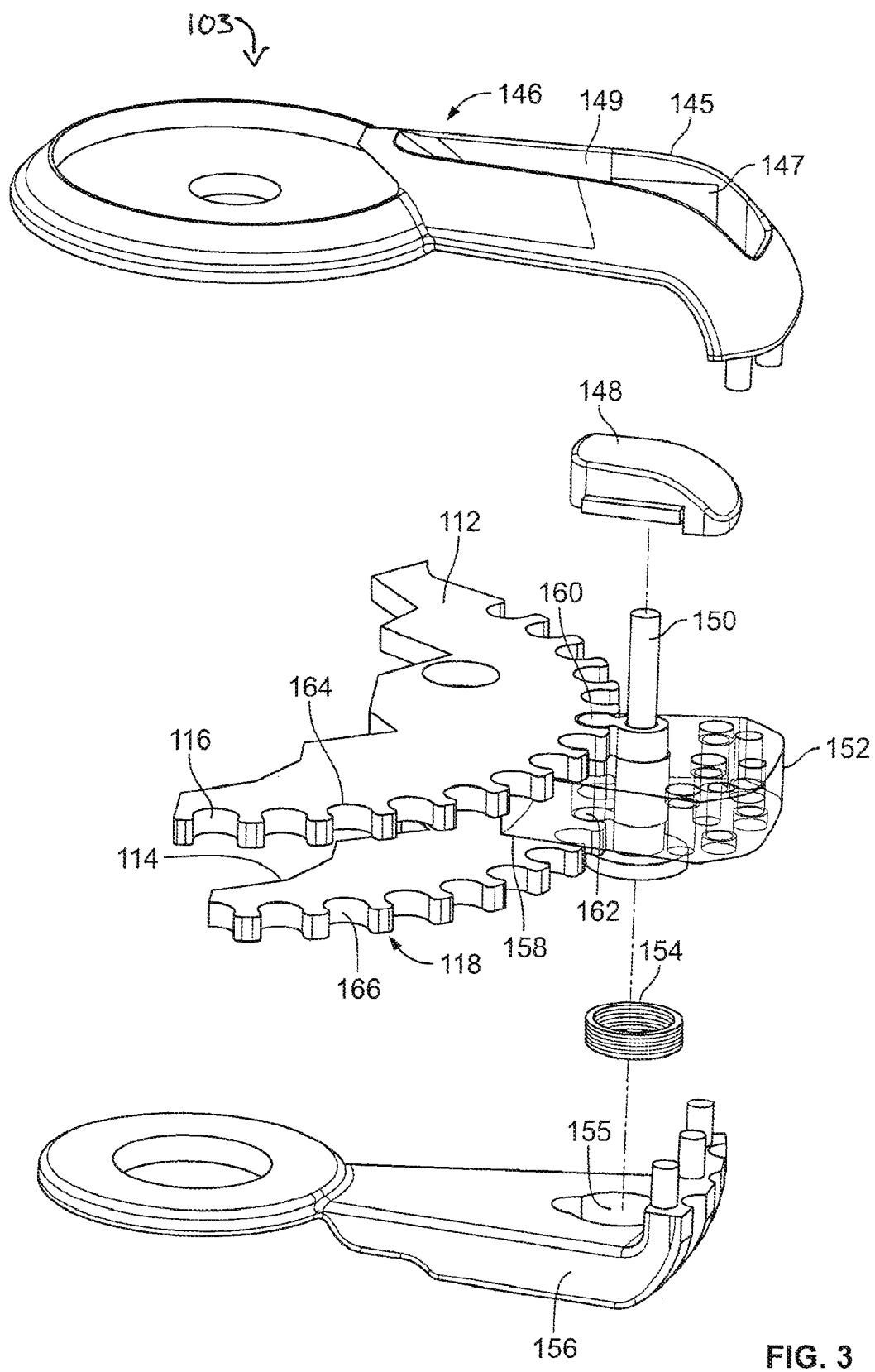
FIGS. 3-4 show exploded views of the first hinge stop assembly of FIG. 1A.
Figure 4:
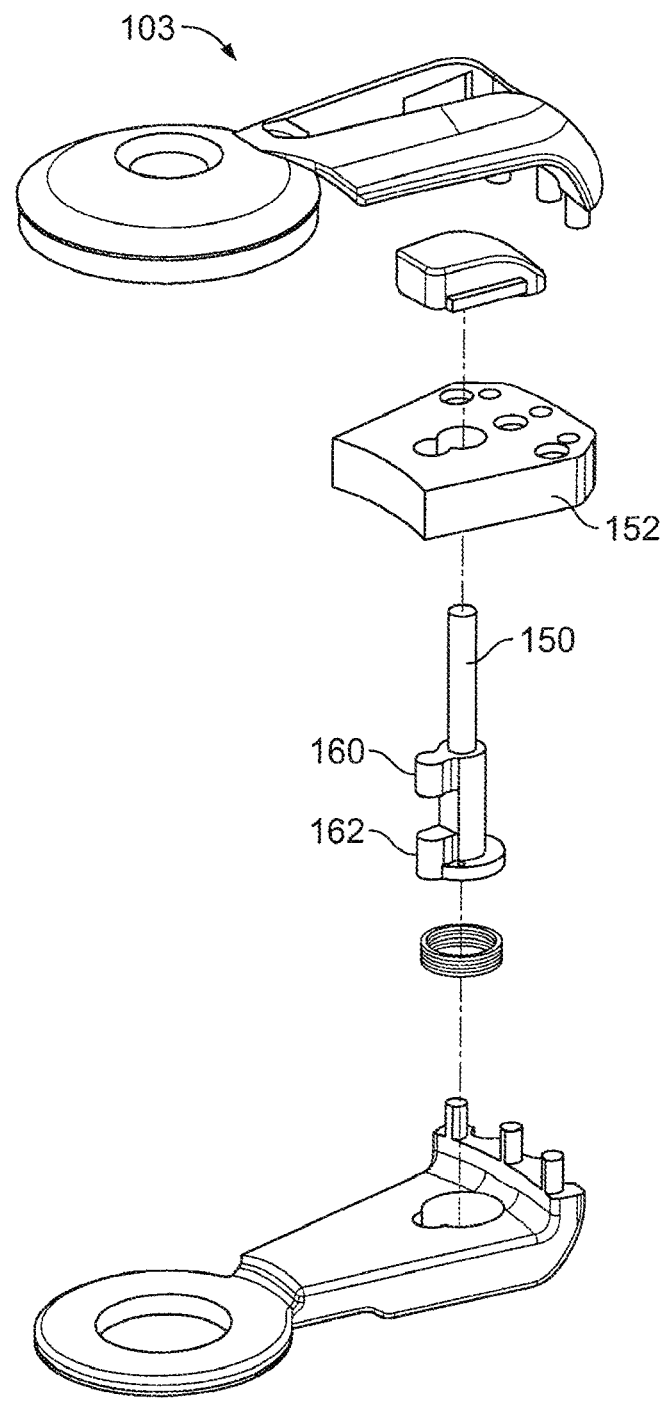

The hinge stop assemblies 103 and 105 positions are adjustable by the engagement and disengagement of the gear teeth 116, 118 of the first and second hinge plates 112 and 114, as shown in FIG. 3. As shown, the hinge stop assembly 103 includes an indexing key 150 that fits within an upper housing 146 and a lower housing 156, a button 148 for actuating the indexing key 150, a hinge stop 152 engaged to the indexing key 150, and a compression spring 154 housed within the lower housing 156 for biasing the indexing key 150. The button 148 is housed within a button groove 147 disposed on the upper housing 146. The button 148 may protrude from a top surface 145 of the upper housing 146 such that the user may tactilely feel the button 148. The button 148 is placed in the "lock" position by engaging the indexing key 150 to the first and second hinge plates 112 and 114. More specifically, as shown in FIG. 4, the indexing key 150 includes an upper key 160 and a lower key 162 for engaging respective grooves 164, 166 of the gear teeth 116 and 118, respectively. When the keys 160 and 162 engage respective gear teeth grooves 164, 166 (FIG. 3), the position of the hinge stop assembly 103 is locked. In that locked position, the hinge stop assembly 103 is unable to move with respect to the first and second hinge plates 112 and 114. To release the hinge stop assembly 103, the user activates the button inwardly (toward the user's leg), which release the keys 160, 162 from their respective grooves 164, 166.

The hinge stop 152 includes a hinge stop surface 158 that contacts a stop surface 172 (FIG. 2) of the second frame member 104 when the second frame member 104 reaches the end of its motion. In operation, the hinge member 104 rotates freely within the range of motion allowed between the hinge stop assemblies 103 and 105. When reaching one of the stop assemblies, i.e. assembly 103, the hinge stop surface 158 butts against the stop surface 172 and stops the member 104 from rotating further. The hinge stop assembly 105 has analogous features, including a hinge stop surface 159 that contacts a stop surface 174 (FIG. 2).

When the user is ready to change the limits of the range of angular motion of the second frame member 104, the user actuates the button 148 inwards in the direction noted by Arrow A (FIG. 5) to "unlock" the hinge stop assembly. This downward movement is perpendicular to the hinge cover 106 and the first and second hinge plates 112 and 116 and parallel to the center rotation axis 101. This movement causes the indexing key 150 to also travel inward, thereby disengaging the upper and lower keys 160 and 162 from the button grooves 164 and 166. The hinge stop assembly 103 is now free to travel along the rotation path 109. Pressing down on the indexing key 150 compresses the compression spring 154 housed within a spring housing 155 (FIG. 3) of the lower housing 156. While the compression spring 154 is depressed, the user rotates the hinge stop assembly 103 to a desired angular location along the rotation path 109. The user then releases the button 148 at a desired angular location, whereupon the compression spring 154 forces the indexing key 150 to move back into the lock position (i.e., the indexing key 150 engages the gear teeth 116, 118). This locks the position of the first stop hinge assembly 103, which now defines a new rotational limit for the second frame member 104. The user may also change the position of the stop hinge assembly 105 in the same manner to further adjust the range of motion window for the second frame member 104.

As shown in FIG. 2, the lateral hinge cover 106 includes numerical markings 142 disposed along the rotation paths 109 and 111 for denoting the maximum extension and flexion limiting angles that the second frame member 104 is allowed to travel. The upper housing 146 includes a marking window 149 (FIG. 3) adapted to display the numerical markings 142. As an example, if the hinge stop assembly 103 is locked at −10 degrees, the second frame member 104 is allowed −10 degree of movement from the rotation axis 151 (see FIG. 1A). The second hinge stop assembly 105 may be positioned anywhere along the rotation path 111 (e.g., 20 degrees to 120 degrees).

Figure 5:
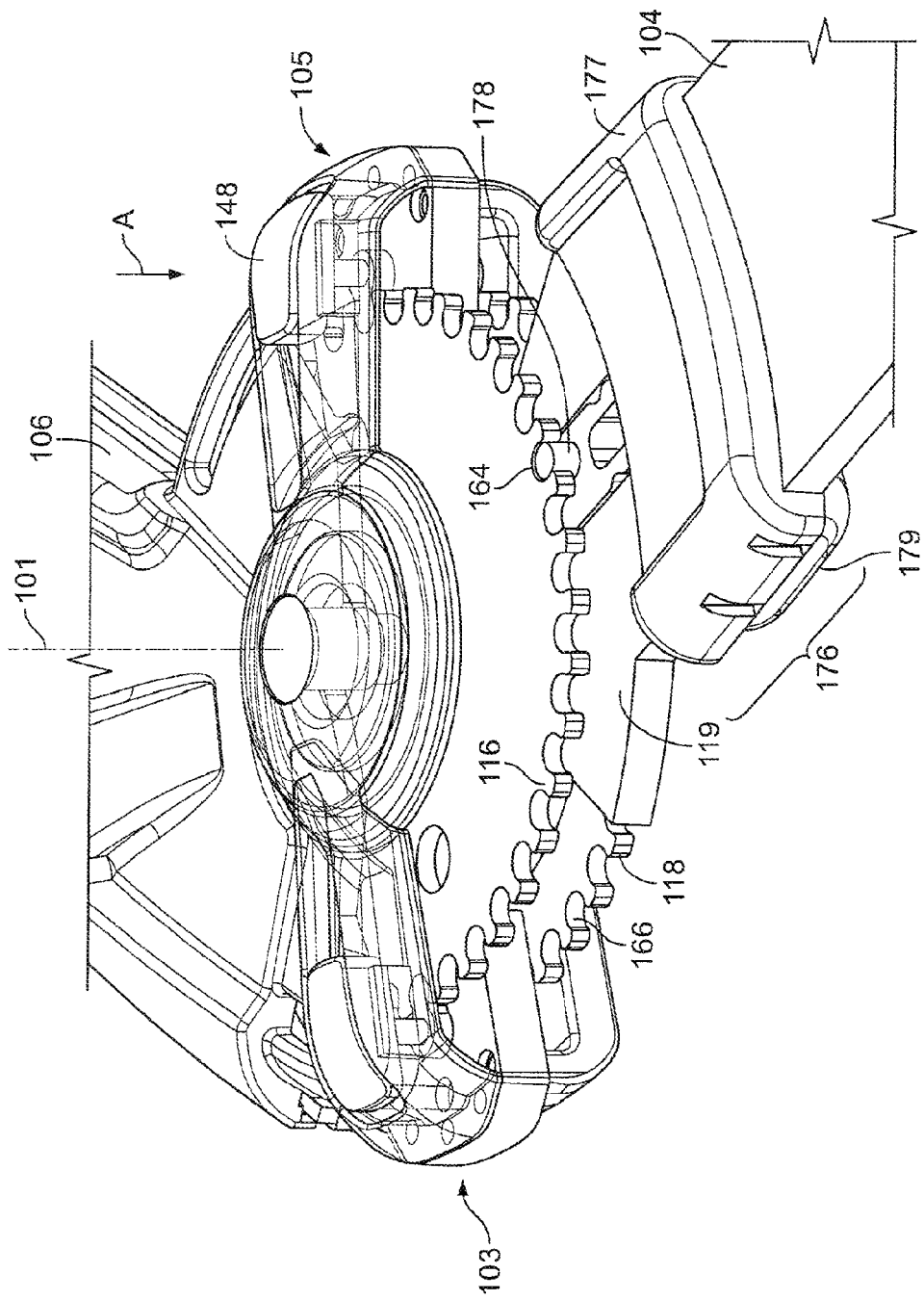
FIG. 5 depicts a perspective view of the hinge of FIG. 1A having a locking mechanism.

The hinge 100 has a low profile, as no buttons protrude radially from the hinge cover 106. This may make it easier for a user to wear the brace under clothing. It may also minimize inadvertent triggering of the buttons 148. As shown in FIG. 5, the button 148 is flush with the top surface of the upper housing 146. Therefore, the user is less likely to accidentally press the button 148. Also the numerical markings 142 are disposed in the same planar orientation as the buttons 148, to minimize confusion.

In certain implementations, the hinge 100 includes a locking mechanism 176 for locking the movement of the second frame member 104 with respect to the first frame member 102. When the locking mechanism 176 is engaged, the hinge 100 is locked and no part of the hinge is able to move. In certain implementations, as illustrated in FIG. 5, the second frame member 104 houses the locking mechanism 176. The locking mechanism 176 includes an upper locking plate 177, a lower locking plate 179 that mates with the upper locking plate, and a locking pin 178 housed within the lower locking plate 179 for engaging the gear teeth 116 and 118. FIG. 2 shows an exploded view of the locking mechanism. As shown, the second frame member 104 includes a groove 180 for receiving a sliding block 181 of the lower locking plate 179. The groove 180 is sized to allow the sliding block 181 to slide back and forth within the groove 180. The sliding block 181 also includes a hole 183 for receiving the locking pin 178. As shown in FIG. 5, when assembled, the upper locking plate 177 and the lower plate 179 movably enclose the second frame member 104. The sliding block 181 may be flush with a top surface 119 of the second frame member 104. When the locking mechanism 176 is activated, the locking pin 178 engages the gear teeth 116 and 118 (FIG. 5), thus the movement of the second frame member 104 is locked to the first and second hinge plates 112 and 114. In this position, a user wearing this brace would not be able to bend his/her leg.

When the user is ready to unlock the hinge 100 to bend the leg, the user pushes the upper locking plate 177 away from the gear teeth 116 and 118 to disengage the locking pin 178 from the grooves 164 and 166. When the locking pin 178 is disengaged from the gear teeth 116 and 118, the second frame member 104 is free to rotate between the first and second stop assemblies 103 and 105.

In certain implementations, the hinge 100 is used in a pelvic or hip brace. The hinge 100 may be used to limit the range of motion of flexion and extension as well as abduction and adduction of a hip joint. The pelvic or hip brace may be worn after injury or post-operatively to reduce incidence of dislocation of the hip.

Figure 6A:
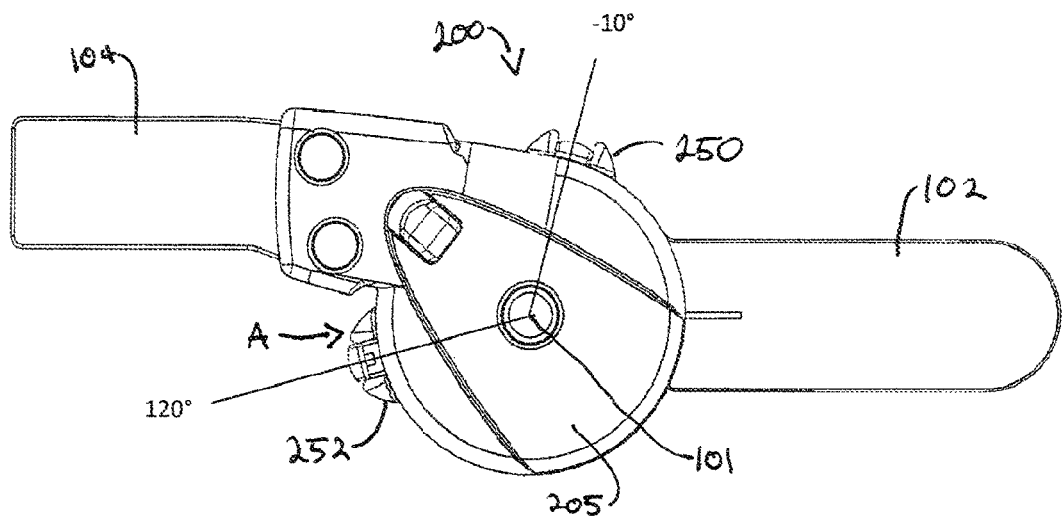
FIGS. 6A-6B depict a hinge having low profile hinge stop assemblies.
Figure 6B:
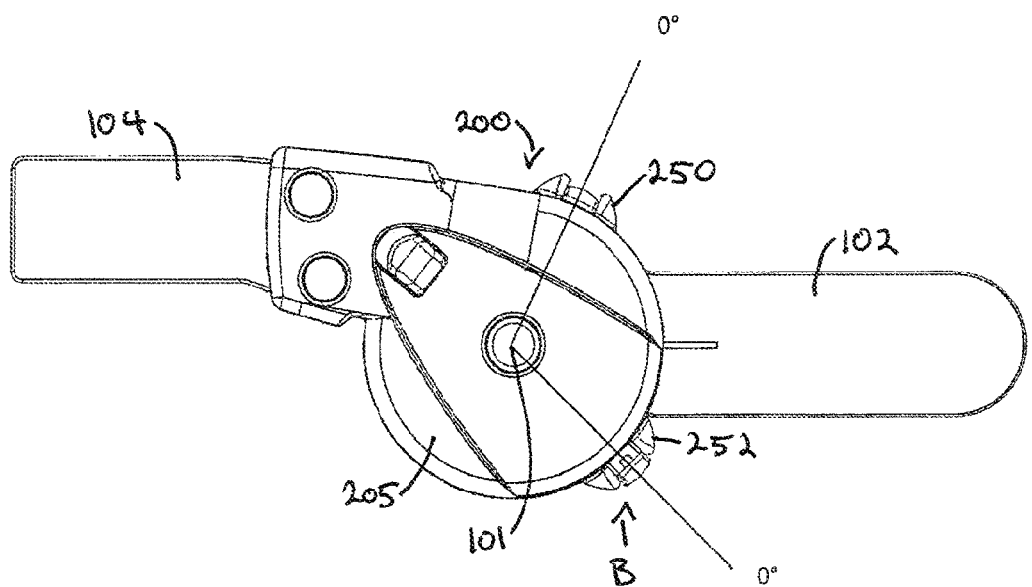

FIG. 6A and FIG. 6B show alternative embodiments of a hinge 200, similar to hinge 100, but with lower profile hinge stop assemblies 250 and 252 that are disposed between lateral hinge plate 205 and a medial hinge plate 207. As shown, similar to hinge 100, the hinge 200 includes a first frame member 102 that is a freely rotating member about the hinge 200, and a second frame member 104 that is fixed with respect to the hinge 200. The lower profile hinge stop assemblies 250 and 252 may be actuated radially and moved angularly within the space between the lateral hinge plate 205 and the medial hinge plate 207. Shown in FIG. 6A, the hinge stop assembly 252 is positioned at Position A, leaving an angle of approximately 120 degrees between the two stop assemblies 250 and 252. In this configuration, the free rotating frame member 102 is allowed to angularly rotate between the hinge stop assembly 250 and the stop assembly 252. As shown in FIG. 6B, the hinge stop assembly 252 is adjusted angularly to reduce the rotational space between the two hinge stop assemblies 250 and 252, thereby confining or even locking frame member 102 between the two hinge stop assemblies. As noted, the hinge stop assembly 250 and 252 are lower profile and actuatable radially, for ease of patient use.

Figure 7:
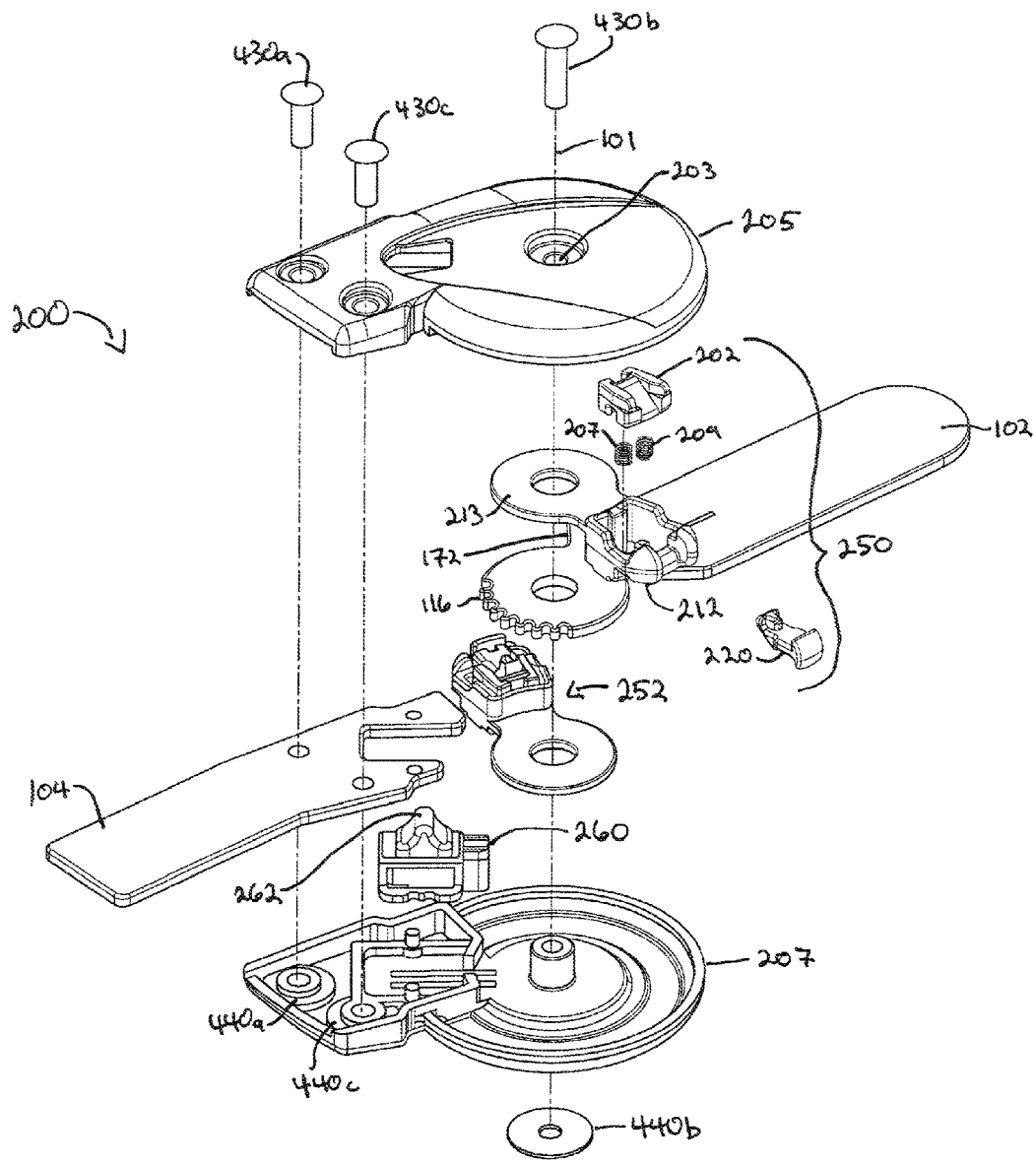
FIG. 7 shows an exploded view of the hinge of FIG. 6A.

FIG. 7 depicts various components of the hinge 200 in an exploded view. Similar to the hinge 100, the lateral and medial hinge plates 205 and 207 and the frame members 102 and 104 are pivotally combined so that they pivot about a central rotational axis 101. Fasteners 430a, 430b, and 430c fasten the components together, and include for example retainers 440a, 440b and 440c to fasten the components together. A locking mechanism 260 having a press button 262 is actuatable with respect to the frame member 104 to lock the frame member 104 and 102 in place. The hinge stop assemblies 250 and 252 shown in FIG. 7 each have a central platform 213, shown in FIG. 8, joined to a hinge stop 212, and an indexing key 202 that is actuatable by a button 220. The button 220 and springs 207 and 209 are configured to allow the hinge stop assembly to move radially inward and downward upon actuation of the indexing key 202, as described more fully below. The frame members 102 and 104 are allowed to rotate with respect to each other until the stop surface 172 of the frame member 102 reaches a hinge stop surface of the hinge stop 212.

Figure 8:
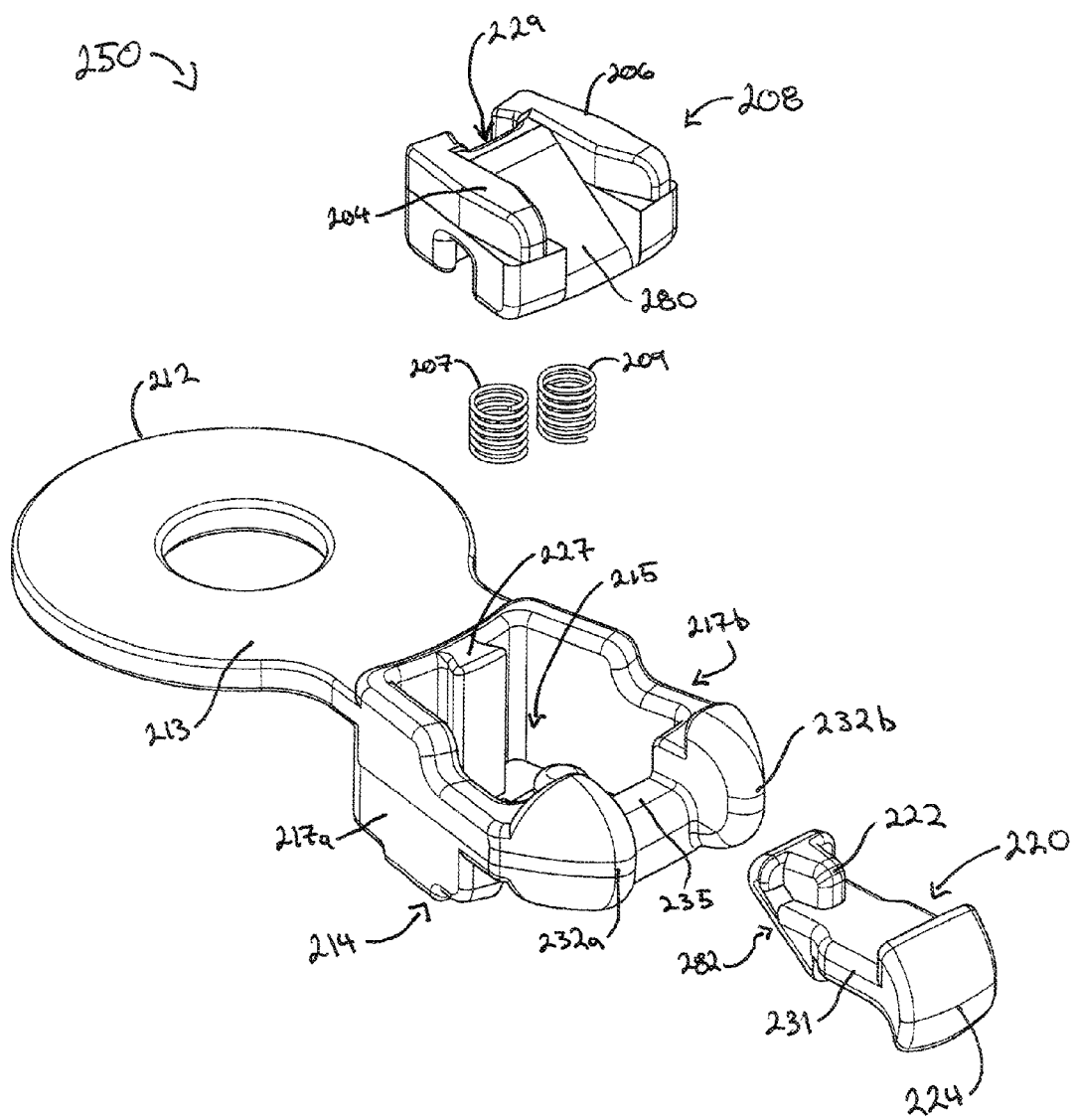
FIGS. 8-9 show components of the hinge of FIG. 6A.

FIG. 8 depicts the components of the hinge stop assembly in further detail. As shown, the hinge stop assembly 250 includes the hinge stop 212 joined to a receptacle 214. The receptacle 214 has an internal cavity 215 and exterior hinge stop surfaces 217a and 217b. The receptacle 214 also includes front shoulders 233a and 233b, forming a trough 235 between them. The receptacle 214 receives the indexing key 208, specifically by tongue 227 of the receptacle sliding within the groove 229 of the indexing key. The indexing key, when seated within the cavity 215, can receive the button 220. As shown, the button 220 has an actuator tip 224 and a nub 222, and the nub 222 fits within notches of the hinge plate to help lock the hinge stop assembly 250. The button 220 also includes a neck portion 231 which, when installed within the hinge stop assembly 250, fits within the trough 235 located between the two shoulders 233a and 233b.

The indexing key 208 includes a ramp 280 that faces radially and angularly away from the center rotational axis that passes through center hole 203. The button 220 includes a complementary sloped interior platform 282 which engages the ramp 280 of the indexing key 208. In particular, the sloped interior platform 282 abuts against the ramp 280 while the hinge is in a locked configuration, but the two surfaces 282 and 280 will slide with respect to each other as the hinge stop assembly 250 is actuated.

Figure 9:
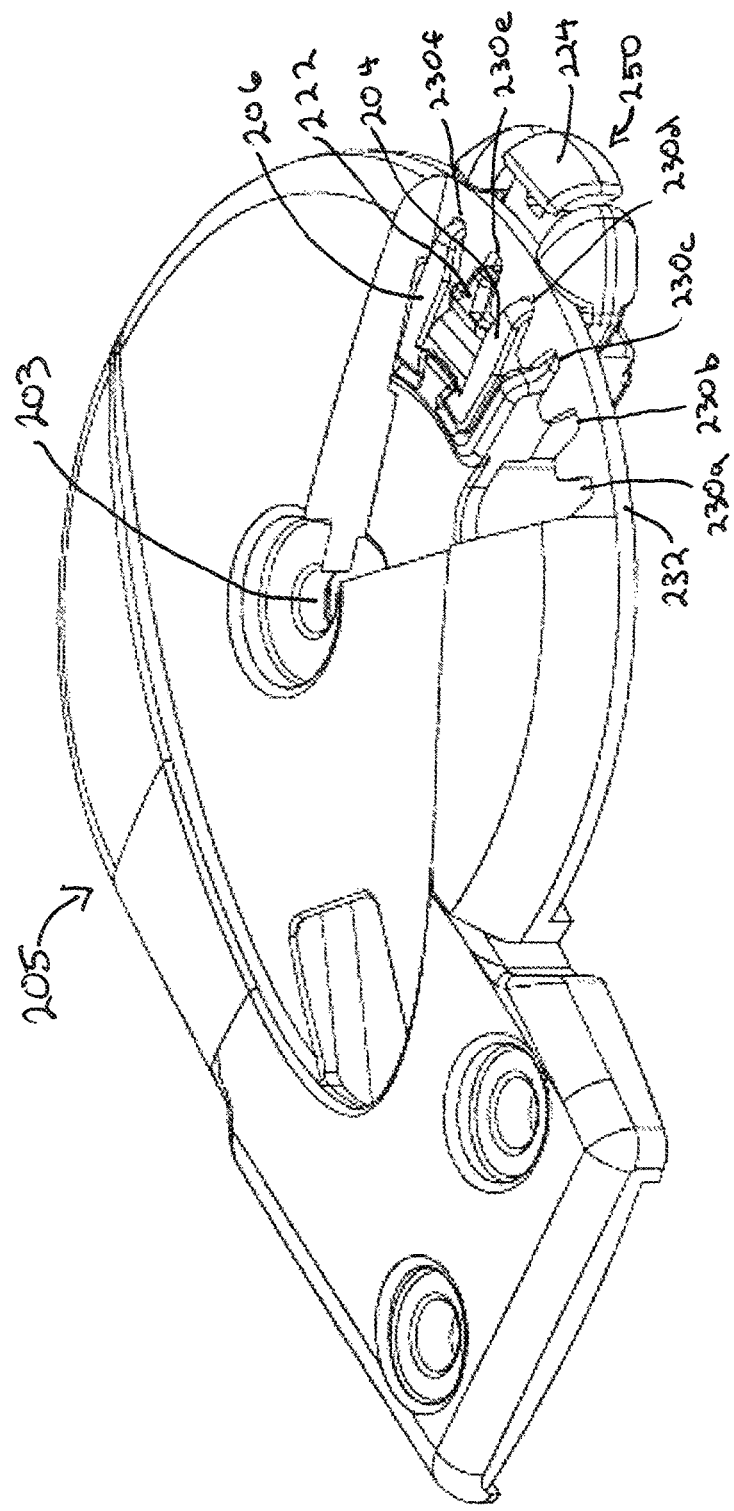

When assembled, the hinge stop assemblies 250 and 252 each fit within notches in the interior surface of the hinge plates. This is shown more particularly in FIG. 9, where the first arm 204 of the indexing key 208 fits within notch 230d disposed within the lateral hinge plate 205. Similarly, the arm 206 of the indexing key 208 fits within the notch 230f, while the nub 222 of the button 220 fits within the notch 230e of the lateral hinge plate 205. As shown the notches 230a-230f are formed within the interior surface rib 232 disposed beneath the lateral hinge plate 205.

Figure 10A:
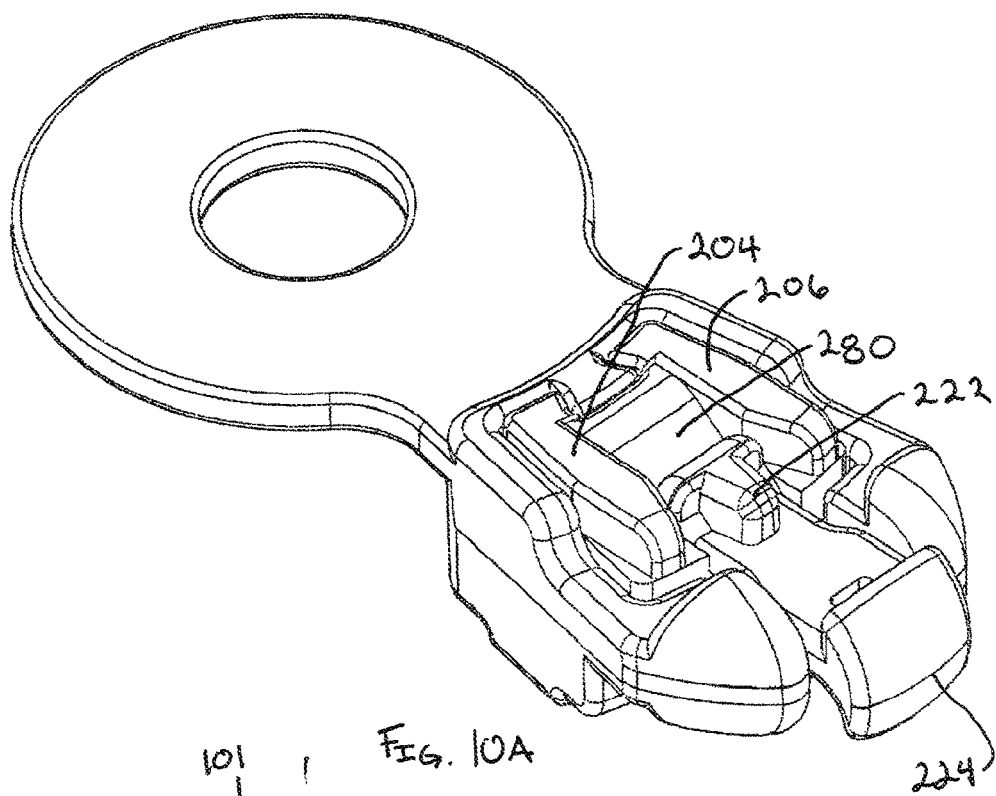
FIGS. 10A-10B show a hinge stop assembly before and after actuation.
Figure 10B:
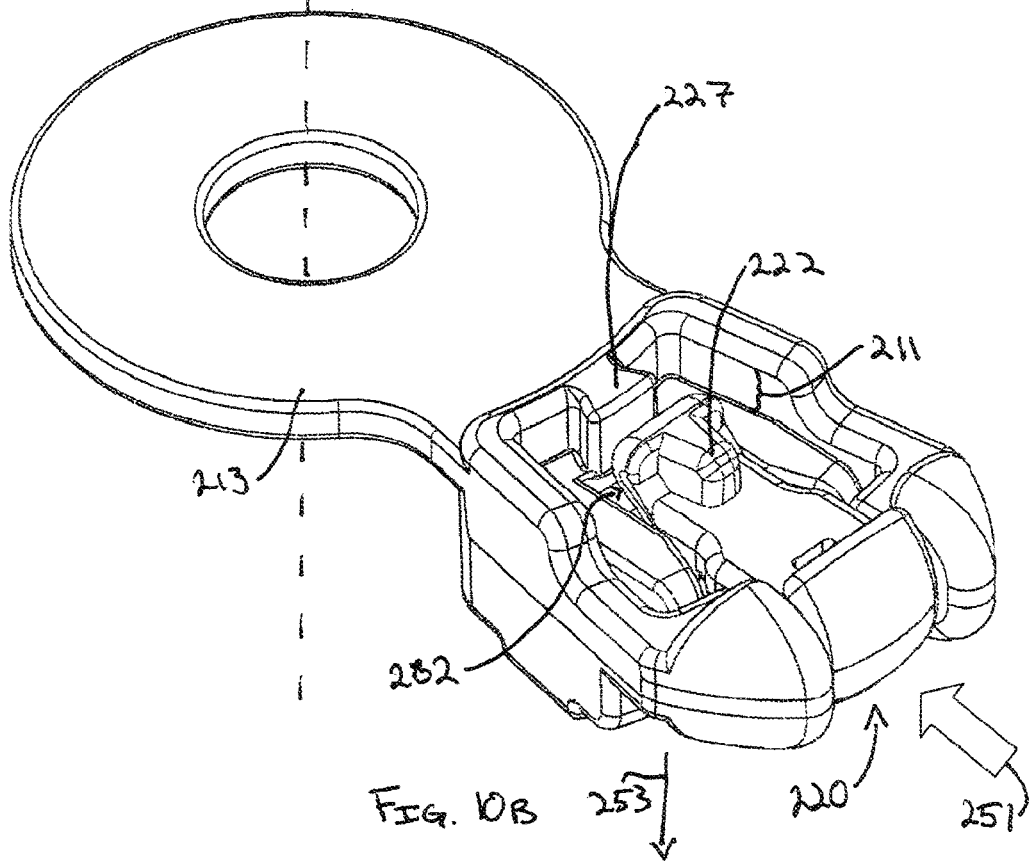

As pointed out above, the button 220 is actuated to release the arms 204 and 206 from their respective notches 230d and 230f within the hinge plate, thereby allowing movement of the hinge stop assembly and adjustment of the angle over which frame members 102 and 104 pivot with respect to each other about the pivot axis 101, which runs through the center hole 203. In particular, as shown in FIGS. 10A and 10B, the actuator 224 is moved radially to unlock the hinge stop assembly by moving the nub 222 and the arms 204 and 206 into the cavity 215 of the receptacle 214. Prior to actuation of the button 220 via actuator 224, as pointed out above, the sloped interior platform 282 rests against the ramp 280 of the indexing key 208. But as shown in FIG. 10B, when the button 220 is actuated radially in the direction of arrow 251, the indexing key 208 drops perpendicularly in the direction of indexing arrow 253, which is parallel to the axis of rotation 101 of the hinge 200, thereby releasing the arms 204 and 206 from their respective notches by dropping them downward, or inward with respect to the side of the patient's knee (i.e. from a right to left or left to right). As shown, the sloped interior platform 282 is pushed radially toward the central platform 213, and the indexing key 208 slides downward, such that the groove 229 slides down the tongue 227, in the direction of arrow 253, leaving a space 211 within the cavity 215, and where the nub 222 approaches the tongue 227. Thus, when the button 220 is actuated radially, the indexing key 208 releases the arms and nub from the notches and allows adjustment of the angle of rotation of the frame member 102 relative to frame member 104.

FIG. 11 depicts the hinge stop assembly 250 having the actuator 224 depressed radially and the indexing key as a consequence being depressed perpendicularly or angularly downward. In this configuration, hinge stop assembly 250 is free to move around the center axis 101 to adjust the limits on the angular rotation of the frame members.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein may be applied to devices, braces, and hinges to be used in other applications.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A hinge assembly for an orthopedic brace, comprising:
   a hinge cover having a center rotation axis;
   first and second frame members pivotably connected to the hinge cover; and
   at least one hinge stop assembly operable with the hinge for limiting rotational travel of the second frame member, the at least one hinge stop assembly having an indexing key that is biased toward a first position and actuatable parallel to the center rotation axis of the hinge to a second position, wherein:
      a rotational limit of the second frame member is locked when the indexing key is in the first position, and the hinge stop assembly is movable around the center rotation axis when the indexing key is in the second position.

2. The hinge assembly claim 1, further comprising a first hinge plate positioned between the hinge cover and the first and second frame members.

3. The hinge assembly of claim 2, wherein the first and second frame members are positioned between the first hinge plate and a second hinge plate.

4. The hinge assembly of claim 3, wherein the first and second hinge plates have gear teeth configured to engage the at least one hinge stop assembly.

5. The hinge assembly of claim 4, wherein the indexing key engages the gear teeth when the indexing key is in the first position.

6. The hinge assembly of claim 4, wherein the at least one hinge stop assembly includes a hinge stop face for making contact with the second frame member, the hinge stop face extending between the first and second hinge plates.

7. The hinge assembly of claim 1, wherein the at least one hinge stop assembly includes an upper housing having a pocket for receiving the button.

8. The hinge assembly of claim 1, comprising a locking mechanism having a locking pin configured to engage gear teeth disposed on first and second hinge plates.

9. The hinge assembly of claim 1, comprising a button that is actuatable in a direction perpendicular to the center rotation axis of the hinge.

10. The hinge assembly of claim 9, comprising a ramp on the indexing key, the ramp facing radially and angularly away from the center rotational axis of the hinge.

11. The hinge assembly of claim 10, wherein the indexing key includes a plurality of arms that fit within corresponding notches disposed within the hinge to form a hinge stop location to limit the angular rotational travel of the second frame member.

12. The hinge assembly of claim 11, further comprising a button wherein the button and indexing key both fit within a receptacle disposed between first and second hinge plates.

13. The hinge assembly of claim 10, wherein the button includes a platform that interfaces with the ramp and that, upon actuation, drives the ramp in a direction that is parallel to the central rotational axis of the hinge assembly.

14. The hinge assembly of claim 9, wherein the indexing key and actuator, when assembled, are disposed between first and second hinge plates, and are actuatable in a direction perpendicular to the central rotational axis of the hinge assembly.

15. A method of adjusting rotation of an orthopedic brace that includes first and second frame members, a hinge having a center rotation axis, and a hinge stop assembly, said method comprising:
   actuating the hinge stop assembly to cause an indexing key to move in a direction parallel to the center rotation axis of the hinge;
   positioning the hinge stop assembly around the hinge; and
   releasing the hinge stop assembly, wherein said releasing causes the indexing key to move in a direction parallel to the center rotation axis of the hinge and lock the hinge stop assembly in position relative to the hinge.

16. The method of claim 15, wherein said actuating comprises applying a force to an actuator button connected to the hinge stop assembly.

17. The method of claim 16, wherein said actuating further comprises applying a force to the actuator button in a direction perpendicular to the center rotation axis of the hinge.

18. The method of claim 16, wherein said actuating further comprises applying a force to the actuator button in a direction parallel to the center rotation axis of the hinge.

19. The method of claim 15, wherein the hinge comprises a hinge plate, and said positioning comprises moving the hinge stop assembly about a perimeter of the hinge plate.

20. The hinge assembly of claim 5, wherein the indexing key disengages the gear teeth when the indexing key is actuated to the second position.

\* \* \* \* \*